United States Patent [19]

Janoff

[11] Patent Number: 5,614,216
[45] Date of Patent: Mar. 25, 1997

[54] SYNTHETIC LUNG SURFACTANT

[75] Inventor: Andrew S. Janoff, Yardley, Pa.

[73] Assignee: The Liposome Company, Inc., Princeton, N.J.

[21] Appl. No.: 442,079

[22] Filed: May 16, 1995

Related U.S. Application Data

[63] Continuation of Ser. No. 90,438, Jul. 9, 1993, abandoned, which is a continuation of Ser. No. 778,728, Oct. 17, 1991, abandoned, which is a continuation-in-part of Ser. No. 599,493, Oct. 17, 1990, abandoned.

[51] Int. Cl.$^6$ .................................................. A61K 9/127
[52] U.S. Cl. ........................... 424/450; 424/43; 514/78; 514/182; 514/958
[58] Field of Search ......................... 424/450, 47, 43; 514/78, 122, 114, 182, 958

[56] References Cited

U.S. PATENT DOCUMENTS

| | | | |
|---|---|---|---|
| 4,312,860 | 1/1982 | Clements et al. | 424/199 |
| 4,571,334 | 2/1986 | Yoshida et al. | 424/95 |
| 4,603,124 | 7/1986 | Takei et al. | 514/78 |
| 4,666,831 | 5/1987 | Janoff et al. | 435/13 |
| 4,698,299 | 10/1987 | Janoff et al. | 435/13 |
| 4,765,987 | 8/1988 | Bonte et al. | 424/450 |
| 4,784,961 | 11/1988 | Russell | 436/63 |
| 4,826,821 | 5/1989 | Clements et al. | 514/78 |
| 4,861,756 | 8/1989 | Jackson | 514/11 |
| 4,915,151 | 4/1990 | Baldeschwieler et al. | 424/450 |
| 4,973,582 | 11/1990 | Yoshida et al. | 514/78 |
| 4,981,690 | 1/1991 | Lopez-Berestein et al. | 424/450 X |

OTHER PUBLICATIONS

Cullis, et al., "Lipid Polymorphism and the Roles of Lipids in Membranes", Chemistry and Physics of Lipids, 40:127–144 (1986).
Cullis, et al. "The Polymorphic Phase Behaviour of Phosphatidylethylanol Amines of Natural and Synthetic Origin," Biochim. Biophys. Acta, 513 (1978) 31–42.
Holm, et al., "Role of Pulmonary Surfactant in the Development and Treatment of Adult Respiratory Distress Syndrome", Anesth. Analg. 1989, 69:805–18.
Shou-Hwa Yu, et a., "Artificial Pulmonary Surfactant", Biochim. Biophys. Acta., (1984) 776:37–47.
Tilcock, "Lipid Polymorphism", Chemistry and Physics of Lipids, 40:109–125 (1986).
Cullis, et al., "Effect of Cholesterol on the Properties of Equimolar Mixtures of Synthetic Phosphatidyethanolamine and Phosphatidylcholine", A $^{31}$P NMR and Differential Scanning Calorimetry Study, BBA, 513 (1978), 21–30.
Harwood, et al., "Lung Surfactant", Biocem. Soc. Transactions, 13(6), pp. 1079–1081 (1985).
Reynolds, et al., "Use of surfactant in the prevention and treatment of neonatel respiratory distrees syndrome", Clinical Pharmacy, 8 (1989), 559–576.

Primary Examiner—Neil S. Levy
Attorney, Agent, or Firm—Kenneth B. Rubin

[57] ABSTRACT

A synthetic lung surfactant composition and process for depositing a monolayer of a phosphatidylcholine lung surfactant to the alveoli of a mammal. The composition comprises a phosphatidylcholine lung surfactant, a phosphatidylethanolamine, and cholesterol in proportions such that the composition is in lamellar form at or below a first temperature and in non-lamellar form at a second temperature which is higher than the first temperature. A preferred phosphatidylcholine lung surfactant for use in this invention is dipalmitoyl phosphatidylcholine (DPPC), which is known to be the major lipid constituent of natural mammalian lung surfactant, and a preferred phosphatidylethanolamine is dioleoyl phosphatidylethanolamine (DOPE). In particular embodiments, the composition is in lamellar form at about room temperature (25° C.), and in non-lamellar form at a temperature in the range of about 30° to 37° C., which is at or below normal human body temperature (37° C.). The composition may also include one or more therapeutic peptides or other pharmaceutical agents. The synthetic lung surfactant may be used to treat a mammal for respiratory distress syndrome caused by an insufficiency of natural lung surfactant.

5 Claims, 2 Drawing Sheets

DOPE-DPPC-CHOL  7:3:3 MOL:MOL

DOPE-DPPC-CHOL 7:3:5 MOL:MOL

DOPE-DPPC-CHOL 7:3:3 MOL:MOL

SYNTHETIC LUNG SURFACTANT

CROSS-REFERENCES TO RELATED APPLICATIONS

This application is a continuation of application Ser. No. 008/090,438 filed on Jul. 9, 1993, now abandoned, which is a continuation of application Ser. No. 07/778,728 filed on Oct. 17, 1991, now abandoned which is a continuation-in-part of application Ser. No. 7/599,493, filed Oct. 17, 1990.

FIELD OF THE INVENTION

This invention relates to lung surfactant, and more particularly to a liposomal lung surfactant which can be used to coat lung alveoli in like manner as natural pulmonary surfactant.

BACKGROUND OF THE INVENTION

In "Artificial Pulmonary Surfactant", *Biochimica et Biophysica Acta*, 776:37–47 (1984), Shou-Hwa Yu et al. describe the natural pulmonary or lung surfactants which coat the alveoli of mammalian lungs. Such surfactants comprise lipids and surfactant-associated proteins. Pulmonary surfactant reduces surface tension at the air-liquid interface of the alveoli. Studies indicate that in the presence of surfactant, the surface tension in normally expanded lungs approximates 30 dyne/cm, while during expiration this value approaches 0 dyne/cm. Presence of pulmonary surfactant is particularly critical at birth, when the newborn infant must clear its lungs of pulmonary fluid and establish regular breathing. Absence of sufficient surfactant stores to maintain a low surface tension during the neonatal period appears to be the major factor associated with the development of the neonatal respiratory distress syndrome, also known as hyaline membrane disease, the principal cause of perinatal mortality and morbidity in developed countries. Treatment of infants suffering from advanced neonatal respiratory distress syndrome with surfactant preparations derived from bovine surfactant lipid extracts has shown a marked improvement in lung expansion and gas exchange. In like manner, a deficiency of lung surfactant in adults can cause adult respiratory distress syndrome (ARDS).

It is generally acknowledged that the ability of pulmonary surfactant to reduce the surface tension of an air/liquid interface to near 0 dyne/cm is dependent upon the formation of a monolayer of relatively pure dipalmitoyl phosphatidylcholine (DPPC) during compression. However, at normal body temperature of 37° C. hydrated bilayers of DPPC exist in the gel state, from which adsorption can occur only very slowly. As a result, attempts to develop artificial mixtures which could function to transfer DPPC to the air/liquid interface at a sufficient rate to maintain normal lung functions have not been successful. One approach towards the formation of artificial surfactants has been to devise methods for dispersing DPPC using long-chain alcohols or inert hydrocarbon oils, or by administering "dry" lipid mixtures in which the DPPC is not fully hydrated.

Another possibility discussed by Yu et al., cited above, is to disperse the DPPC with other lipids which promote the formation of the hexagonal $H_{II}$ phase. This latter state consists of elongated cylinders of lipids in inverted micellar form with the fatty acids extending outwards and the polar head-groups binding an inner core or pore of water which extends along the elongated cylinder. Because air is more hydrophobic than water, it is postulated by Yu et al. that a cylinder of $H_{II}$ phase interacting with the air/liquid interface could tend to unfold, thereby transferring many lipid molecules to a surface. However, because of the thick gel-like consistency of hexagonal $H_{II}$ DPPC, it is not believed that DPPC in this form could be effectively administered in vivo to deposit a surfactant monolayer on alveoli surfaces.

When administering DPPC to alveoli as a lung surfactant, it is important that the DPPC form a monolayer spread over as much of the alveoli surface area as possible, to provide maximum treatment to the lung. Furthermore, the rate of monolayer deposition may be critical in the treatment of a subject with breathing difficulties brought on by respiratory distress syndrome. The prior methods for delivering DPPC to lung alveoli have not been able to deposit an effective surfactant monolayer of DPPC to the alveoli surfaces. When DPPC in bilayer form has been administered to alveoli, the spreading rate has been found to be too slow to form an effective monolayer or to provide adequate relief for breathing difficulties. Similarly, as discussed above, the thick gel-like consistency of DPPC in hexagonal $H_{II}$ form is believed to make it unsuitable for forming a monolayer on alveoli surfaces.

SUMMARY OF THE INVENTION

In accordance with the present invention a synthetic lung surfactant composition is provided for depositing a monolayer of a phosphatidylcholine lung surfactant to the alveoli of a mammal. The composition comprises a phosphatidylcholine lung surfactant, a phosphatidylethanolamine, and cholesterol in proportions such that the composition is in lamellar form at or below a first temperature and in non-lamellar form at a second temperature which is higher than the first temperature. A preferred phosphatidylcholine lung surfactant for use in the present invention is dipalmitoyl phosphatidylcholine (DPPC), which is known to be the major lipid constituent of natural mammalian lung surfactant, and a preferred phosphatidylethanolamine is dioleoyl phosphatidylethanolamine (DOPE). In particular embodiments, the first temperature is about room temperature (25° C.), while the second temperature is at or near the body temperature of the mammal being treated, which for humans would be in the range of about 30° to 37° C. In a particular embodiment of the present invention, the composition comprises about 3 parts DPPC to about 7 parts DOPE to about 5 to 10 parts cholesterol, all parts by molar ratio. (Unless otherwise indicated, throughout this application all parts and percentages are by molar ratio.)

In a further embodiment, the composition of the present invention may include one or more therapeutic peptides, such as surfactantassociated proteins. Such proteins can be either naturally derived or synthetic. The composition may also include one or more additional pharmaceutical agents.

Another embodiment of the invention is a method of depositing a monolayer of DPPC on the surface of lung alveoli by dispersing the composition of the invention directly into the lungs in the area of the alveoli.

A further embodiment of the invention is a method for treating respiratory distress syndrome caused by an insufficiency of natural lung surfactant in a mammal, the method comprising the administration of the composition of the present invention to the alveoli of the mammal being treated. Such administration may be effected by well-known methods of pulmonary administration such as intubation or inhalation.

In accordance with a further embodiment of the invention, there is provided a pharmaceutical formulation suitable for intubation, inhalation or other means of pulmonary administration, comprising the synthetic lung surfactant composition of the present invention in association with pharmaceutical carriers or diluents. There is also provided a process for the manufacture of such a pharmaceutical formulation, the process comprising combining phosphatidylcholine lung surfactant, phosphatidylethanolamine, and cholesterol to form the artificial lung surfactant composition of the present invention, and mixing the composition with pharmaceutical carriers or diluents to produce a formulation suitable for pulmonary administration.

DETAILED DESCRIPTION OF THE INVENTION

Figure 1:
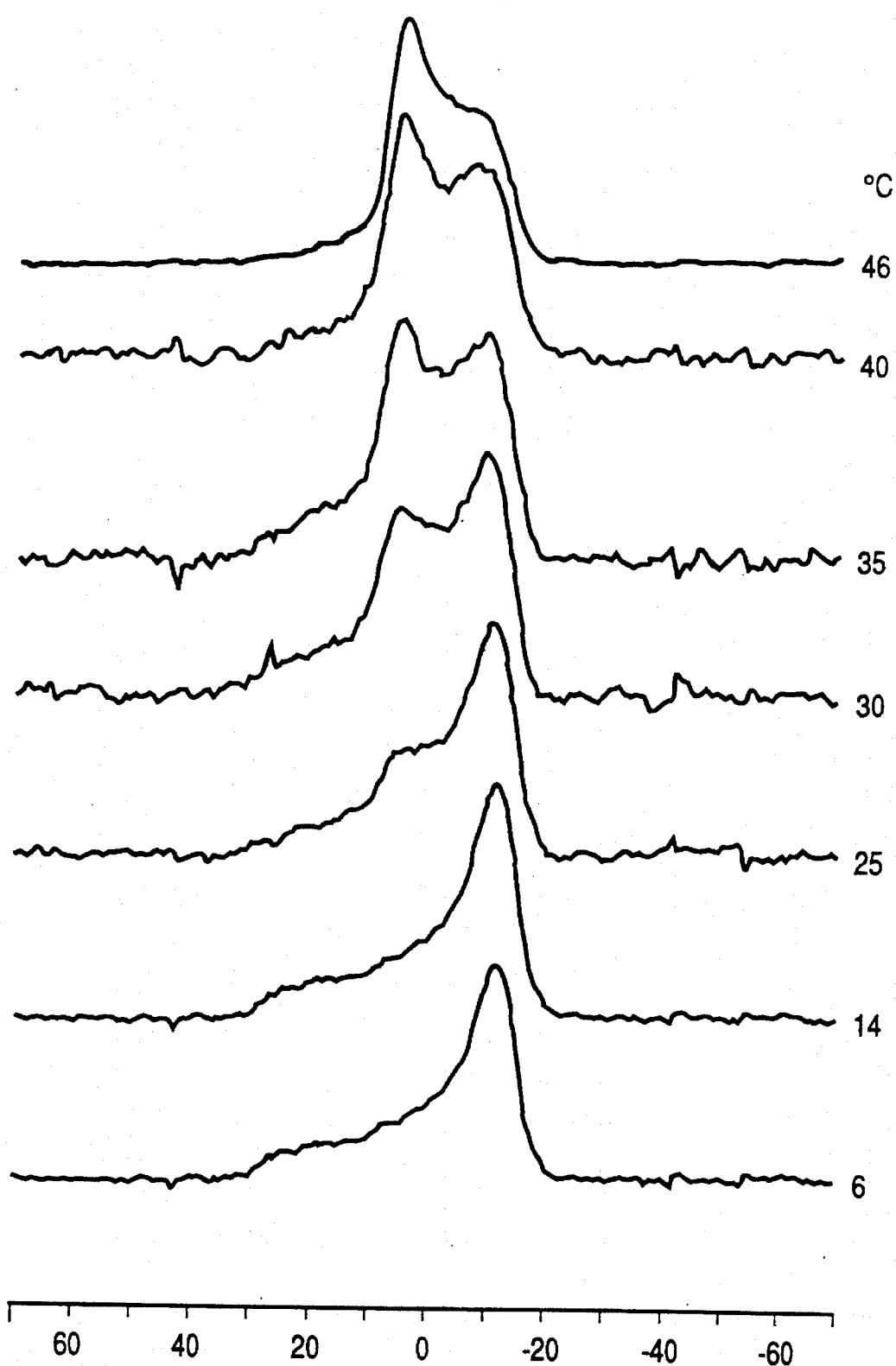
FIG. 1 is a graphical representation of the results of 360-MHz $^{31}$P-NMR spectra measured at temperatures ranging from 6° to 46° C. for a sample of lung surfactant made in accordance with the present invention, comprising DOPE-DPPC-Cholesterol in a 7:3:10 molar ratio.

The present invention stems from the discovery that when a phosphatidylcholine (PC) lung surfactant passes from bilayer form to hexagonal $H_{II}$ or other non-bilayer form, the PC passes through a disordered intermediate phase. This intermediate phase generates monomers which spread rapidly over a hydrous surface causing a rapid reduction in surface tension. For example, the bilayer and hexagonal $H_{II}$ forms of dipalmitoyl phosphatidylcholine (DPPC) are both very stable, while the disordered intermediate phase only exists for a brief time until the DPPC can reform into one of its stable forms. The key to the present invention is devising a means to cause the PC to pass through the monolayer transition phase while in situ at the surface of lung alveoli. If this can be achieved, then the PC will spread rapidly over the alveoli surface while in its disordered monomer form.

Certain phosphatidylethanolamines (PEs) are known to be polymorphic, having both lamellar and a hexagonal $H_{II}$ forms. Furthermore, such PEs are known to transform from their lamellar form to their hexagonal $H_{II}$ form with increasing temperature. (See Tilcock, "Lipid Polymorphism", Chemistry and Physics of Lipids, 40:109, 110–111 (1986).) Cholesterol is known, in general, to have a destabilizing effect on bilayer forms of lipids.

In the present invention a PC lung surfactant is combined with a PE, and with a small amount of cholesterol, in suitable proportions to form a synthetic lung surfactant composition which is in stable bilayer form at a first temperature and which passes through a disordered transition phase to hexagonal $H_{II}$ or other non-lamellar form at a second, higher temperature. For use as a synthetic lung surfactant, the first temperature is preferably about room temperature (25° C.), while the second temperature is at or near the body temperature of the mammal being treated, which for humans would preferably be in the range of about 30° to 37° C.

A preferred phosphatidylcholine lung surfactant for use in the present invention is dipalmitoyl phosphatidylcholine (DPPC), which comprises two fully saturated C16 "tail" groups on a PC "head" group. Other PCs which may be used as the PC lung surfactant include dimyristoyl phosphatidylcholine (DMPC) (C14 tail groups) and distearoyl phosphatidylcholine (DSPC) (C18 tail groups).

A preferred phosphatidylethanolamine for use in the present invention is dioleoyl phosphatidylethanolamine (DOPE), which is chemically compatible with DPPC, which is biologically safe for use in the lungs, and which produces a composition with the desired temperature-dependent phase transition properties. However, any chemically compatible and biologically safe phosphatidylethanolamine which can combine with a selected phosphatidylcholine lung surfactant to give the desired temperature-dependent phase transition may be used.

For compositions comprising DPPC and DOPE, good results are obtained using these components in molar ratios of about 2 to 4 parts DPPC to about 8 to 6 parts DOPE, preferably about 3 parts DPPC to about 7 parts DOPE, to obtain the desired phase transition temperature.

The third component of the composition is cholesterol (CHOL), which is known for its effectiveness in disrupting lipid bilayers. In the present composition, the cholesterol is believed to destabilize the relatively stable lamellar phase, so that the lung surfactant enters an unstable disordered intermediate phase at the desired temperature. Good results are obtained using a molar ratio of about 5 to 10 parts cholesterol to 10 parts of combined phosphatidylcholine and phosphatidylethanolamine.

The composition of the present invention may also include one or more therapeutic peptides, such as surfactant-associated surface active proteins. Such proteins can be either naturally derived or synthetic. Of particular interest are those proteins which are found in natural lung surfactants, or synthetic peptides which mimic such proteins. Some of these surfactant-associated proteins have been found to be enriched in positively charged amino acid groups, and to contain both hydrophobic and hydrophilic peptide groups.

Among the synthetic peptides which have been found useful in the lung surfactant compositions of the present invention are those comprising the peptides Arginine (abbreviated "R"), which is hydrophobic in character, and Leucine (abbreviated "L"), which is hydrophilic in character. A particularly useful synthetic peptide for use in the surfactants of the present invention is denominated $RL_4$ and consists of Arginine and Leucine groups in the configuration:

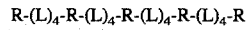

R-(L)$_4$-R-(L)$_4$-R-(L)$_4$-R-(L)$_4$-R

For the tests discussed below, $RL_4$ peptide was obtained from the Research Institute of Scripps Clinic, La Jolla, Calif.

The compositions of the present invention may also include one or more additional other pharmaceutical agents.

EXAMPLE 1

To exhibit the temperature-dependent polymorphic properties of the composition of the present invention, a sample was made comprising DOPE-DPPC-CHOL in a molar proportion of 7:3:10, using 55.4 g of DOPE, 23.4 g of DPPC, and 41.2 g of cholesterol. The DOPE and DPPC were obtained from Avanti Polar Lipids, Birmingham, Ala.; and the cholesterol from Baker Chemicals. The material was dried to a thin film from a chloroform mixture using rotoevaporation, and suspended in 6 ml of 10 mM HEPES buffer with 150 mM sodium chloride at a pH of 7.4.

FIG. 1 shows 360-MHz $^{31}$P-NMR spectra measured at temperatures ranging from 6° to 46° C. The change in shape of the graph lines as temperature increases is indicative of a transformation of the composition from lamellar phase to hexagonal $H_{II}$ phase. This type of spectra data and its significance to lipid phases is discussed at length in Tilcock, cited above. At room temperature, 25° C., the composition is still in lamellar form, while at 40° C. it has clearly shifted to a wave pattern characteristic of $H_{II}$ phase. At 35° C., which is just below normal body temperature, the pattern is believed to show a transition stage, in which both lamellar and $H_{II}$ phase are present.

EXAMPLE 2

Two additional samples of lung surfactant compositions were made using the materials and procedures of Example 1. Sample 2 was a DOPE-DPPC-CHOL composition in a molar ratio of 7:3:5, containing 66.9 g DOPE, 28.3 g DPPC, and 24.8 g cholesterol, suspended in 6 ml buffer. Sample 3 was a DOPE-DPPC-CHOL composition in a molar ratio of 7:3:3, containing 30.4 g DOPE, 12.9 g DPPC, and 6.8 g cholesterol, suspended in 2 ml buffer.

Figures 2A, 2B:
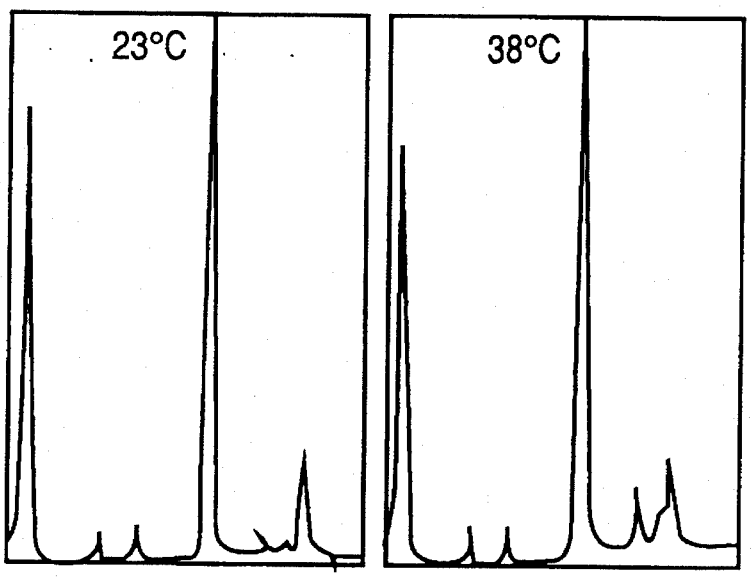
FIGS. 2A and 2B are graphical representations of the results of small-angle X-ray diffraction intensity (arbitrary units) versus inverse reciprocal distance, measured at 23° C. and 38° C., for a sample of lung surfactant made in accordance with the present invention, comprising DOPE-DPPC-Cholesterol in a 7:3:5 molar ratio.
Figures 3A, 3B:
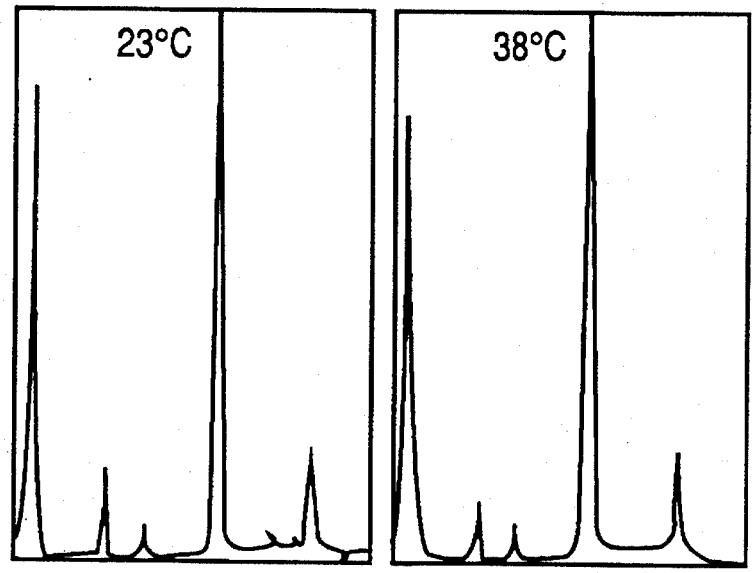
FIGS. 3A and 3B are graphical representations of the results of small-angle X-ray diffraction measurements at 23° C. and 38° C. for a comparative example, not made in accordance with the present invention, comprising DOPE-DPPC-Cholesterol in a 7:3:3 molar ratio.

Both samples were tested by small angle X-ray diffraction, and the results are shown in FIGS. 2A and 2B, and 3A and 3B. In each figure, the graph A on the left represents the results for the sample at 23° C., and the graph B on the right represents the results for the sample at 38° C. The phase of a given sample can be determined by examining the right side of a given graph. FIGS. 2A and 3A both show a single peak at the right of the tall peak near the center of each graph. This double peak is a signature indicative of lipids in a lamellar phase. FIG. 3B also shows this same signature, indicating that at 38° C. Sample 3 is still in a lamellar phase. FIG. 2B shows a distinct double peak at the same location on the right side of the graph. This is a signature which is at least indicative of a change out of the lamellar phase, and may represent a transition to hexagonal $H_{II}$ phase. From these results, it may be seen that the composition containing 3 parts of cholesterol was still in the lamellar phase at a temperature of 38° C., while the composition containing 5 parts cholesterol clearly shows a transition out of the lamellar phase at or below 38° C.

EXAMPLE 3

Tests were conducted to determine the effectiveness of the lung surfactants of the present invention in the treatment of breathing problems associated with premature birth. As discussed above, lung surfactant is particularly critical at birth, when a newborn infant must clear its lungs of pulmonary fluid and establish regular breathing. A deficiency of lung surfactant at this critical stage can result in severe breathing difficulties and even death.

In the present tests, premature fetal rabbits were used as a model of lung surfactant insufficiency, such rabbits being known to have difficulty initiating breathing due to a low level of natural lung surfactant. In each case, the fetal rabbit was administered a 0.2 ml or 0.3 ml test surfactant, ventilated, and monitored for breathing. After 30 minutes, the animal was examined for quality of breathing and color, with a healthy pink color being indicative of good breathing. In addition, lung volume and airway pressure were measured, and these results used to calculate dynamic compliance, expressed in arbitrary units as a ratio of flow to pressure per unit of body weight. The higher the value of the measured compliance, the better the breathing of the test animal. These test procedures are discussed further in Revak, et al., "Reconstitution of surfactant activity using purified human apoprotein and phospholipids measured in vitro and in vivo", *Am. Rev. Respir. Dir.* 134:1258–1265 (1986).

Tests were conducted using 7:3:10 DOPE-DPPC-Cholesterol surfactant made in accordance with Example 1, above (Sample A), and 7:3:5 DOPE-DPPC-Cholesterol surfactant made in accordance with Example 2 (Sample B).

As discussed above, the compositions of the present invention can also include one or more therapeutic proteins. Lung surfactants in accordance with the present invention were made from soy phosphatidylcholine (soy PE), DPPC, and cholesterol in combination with the peptide $RL_4$, discussed above. Samples of peptide-containing surfactants were prepared comprising soy PE-DPPC-cholesterol in a 7:3:3 ratio and containing 3% by weight $RL_4$ peptide (Sample C), and soy PE-DPPC-cholesterol in a 7:3:5 ratio, containing 3% by weight $RL_4$ peptide (Sample D). Samples C and D were also included in the present fetal rabbit model tests.

Additional tests were conducted using 150 mM saline solution as a negative control, and native human surfactant, isolated from term amniotic fluid, as a positive control.

Three set of tests were conducted using the example surfactants and the negative and positive controls. In the first two sets of tests, 0.2 ml doses were administered, while in the third set of tests 0.3 ml doses were used. In the tests in which the animals were administered example surfactants Samples A, B, C, or D, or the human surfactant positive control, all showed excellent breathing within 2 to 3 minutes of ventilation, and all acquired a healthy pink color. At the end of the 30-minute test periods, all of these animals continued to show good breathing and healthy pink color. The rabbits administered the saline negative control had difficulty breathing, and did not have a healthy pink color after 30 minutes. These tests demonstrated that example surfactants Samples A, B, C and D, all made in accordance with the present invention, exhibited comparable results to native human surfactant in treating the respiratory problems associated with an insufficiency of natural lung surfactant.

Compliance values for each animal were measured at periodic intervals over the course of the 30-minute tests. The compliance results are presented in Table 1, with the compliances expressed in arbitrary units as discussed above. The compliance values of the animals administered the example surfactants Samples A, B, C, and D, and the human surfactant positive controls were all at least 25–300% higher that those of the saline negative control animals.

In accordance with another aspect of the present invention, a pharmaceutical formulation suitable for intubation, inhalation or other means of pulmonary administration, comprises the synthetic lung surfactant composition of the present invention in association with appropriate pharmaceutical carriers or diluents. A process for the manufacture of such a pharmaceutical formulation comprises combining phosphatidylcholine lung surfactant, phosphatidylethanolamine, and cholesterol to form the artificial lung surfactant composition of the present invention, and mixing the thus-formed composition with the pharmaceutical carriers or diluents.

The terms and expressions which have been employed are used as terms of description and not of limitation, and there is no intention in the use of such terms and expression of excluding any equivalents of the features shown and described or portions thereof, but it is recognized that various modifications are possible within the scope of the invention claimed.

TABLE 1

Lung Compliance of Premature Fetal Rabbits
Constant Volume Ventilation

|  |  |  |  |  |  |
|---|---|---|---|---|---|
| Set 1 | Sample A | 113 (11 min) | 99 (21 min) | 102 (28 min) |  |
|  | Sample B | 97 (5 min) | 97 (12 min) | 101 (17 min) | 185 (29 min) |
|  | Sample C | 94 (3 min) | 95 (16 min) | 91 (22 min) | 103 (25 min) |
|  | Sample D | 98 (3 min) | 80 (16 min) | 87 (21 min) | 85 (33 min) |
|  | Saline (− con.) | 26 (10 min) | — | — | — |
|  | Human Surf. (+ con.) | 74 (6 min) | 84 (9 min) | 166 (18 min) | 212 (21 min) |
|  | Sample A | 97 (4 min) | 94 (9 min) | 106 (19 min) | 107 (34 min) |
|  | Sample B | 123 (7 min) | 183 (15 min) | 631 (21 min) | 268 (29 min) |
|  | Sample C | 92 (8 min) | 104 (18 min) | 92 (25 min) | 92 (32 min) |
|  | Sample D | 70 (7 min) | 84 (15 min) | 90 (23 min) | 95 (30 min) |
|  | Saline (− con.) | 52 (5 min) | 79 (11 min) | 75 (28 min) |  |
| Set 2 | Sample A | 95 (12 min) | 87 (20 min) | 102 (51 min) |  |
|  | Sample B | 105 (15 min) | 95 (23 min) | 106 (30 min) |  |
|  | Sample C | 123 (12 min) | 115 (30 min) |  |  |
|  | Sample D | 438 (10 min) | 339 (22 min) | 310 (27 min) | 241 (32 min) |
|  | Saline (− con.) | 61 (7 min) | 86 (19 min) | 73 (25 min) | 63 (36 min) |
|  | Human Surf. (+ con.) | 104 (10 min) | 138 (19 min) | 142 (30 min) | 108 (36 min) |
| Set 3 | Sample A | 88 (17 min) | 80 (25 min) | 86 (36 min) |  |
|  | Sample B | 354 (11 min) | 92 (17 min) | 270 (33 min) | 114 (44 min) |
|  | Sample C | 126 (9 min) | 127 (15 min) | 115 (28 min) |  |
|  | Sample D | 93 (10 min) | 95 (18 min) | 84 (30 min) |  |
|  | Saline (− con.) | 31 (9 min) | 55 (18 min) | 41 (30 min) |  |
|  | Human Surf. (+ con.) | 56 (6 min) | 53 (14 min) | 56 (21 min) | 60 (29 min) |
|  | Human Surf. (+ con.) | 84 (9 min) | 78 (18 min) | 90 (30 min) |  |
|  | Sample D | 102 (8 min) | 108 (20 min) | 103 (24 min) | 96 (30 min) |

For Set 1 and 2, 0.2 ml of sample was given.
For Set 3, 0.3 ml of sample was given.
A = DOPE/DPPC/Chol 7:3:10
B = DOPE/DPPC/Chol 7:3:5
C = Soy PE/DPPC/Chol 7:3:3 + 3% by weight RL4
D = Soy PE/DPPC/Chol 7:3:5 + 3% by weight RL4

I claim:

1. A pharmaceutical composition comprising:
   (a) a pharmaceutically acceptable carrier for administration to a mammal by inhalation, intubation or direct pulmonary administration; and,
   (b) a surfactant comprising a lipid component which comprises:
      (i) dipalmitoyl phosphatidylcholine (DPPC);
      (ii) a phosphatidylethanolamine; and,
      (iii) cholesterol,
   wherein dipalmitoyl phosphatidylcholine and the phosphatidylethanolamine are in the surfactant in a ratio of 2–4 moles of dipalmitoyl phosphatidylcholine per 6 to 8 moles of the phosphatidylethanolamine, wherein cholesterol is in the surfactant in a ratio of 5–10 moles per 10 moles of dipalmitoyl phosphatidylcholine plus the phosphatidylethanolamine, wherein the phosphatidylethanolamine has both a lamellar phase and a hexagonal phase, wherein the phosphatidylethanolamine and DPPC are in a bilayer form at the temperature of administration to the mammal and wherein DPPC transforms at the temperature of the mammal's alveoli into a monolayer transitional phase.

2. The composition of claim 1, wherein the phosphatidylethanolamine is dioleoyl phosphatidylethanolamine.

3. The composition of claim 1, wherein the surfactant further comprises a surfactant-associated surface active protein containing hydrophilic and hydrophobic peptide groups.

4. A method of depositing a surfactant on a mammal's alveolar surfaces which comprises administering the composition of claim 1 to the mammal by inhalation, intubation or direct pulmonary administration.

5. The method of claim 4, wherein the mammal is afflicted with a respiratory distress syndrome characterized by a deficiency of natural lung surfactant.

* * * * *